US011219426B2

(12) United States Patent
Zhu et al.

(10) Patent No.: US 11,219,426 B2
(45) Date of Patent: Jan. 11, 2022

(54) METHOD AND SYSTEM FOR DETERMINING IRRADIATION DOSE

(71) Applicant: TUMOR HOSPITAL OF SHANDONG FIRST MEDICAL UNIVERSITY (SHANDONG CANCER HOSPITAL AND INSTITUTE), Jinan (CN)

(72) Inventors: Jian Zhu, Jinan (CN); Zhen Hou, Jinan (CN); Zhenjiang Li, Jinan (CN); Haining Yu, Jinan (CN); Tong Bai, Jinan (CN); Yong Yin, Jinan (CN); Baosheng Li, Jinan (CN)

(73) Assignees: Jinming Yu, Jinan (CN); Tumor Hospital of Shandong First Medical University (Shandong Cancer Hospital and Institute, Jinan (CN)

( * ) Notice: Subject to any disclaimer, the term of this patent is extended or adjusted under 35 U.S.C. 154(b) by 38 days.

(21) Appl. No.: 16/038,440

(22) Filed: Jul. 18, 2018

(65) Prior Publication Data
US 2019/0350550 A1 Nov. 21, 2019

(30) Foreign Application Priority Data
May 18, 2018 (CN) .......................... 201810480047.0

(51) Int. Cl.
A61B 6/00 (2006.01)
A61B 5/00 (2006.01)
(Continued)

(52) U.S. Cl.
CPC .......... *A61B 6/5294* (2013.01); *A61B 5/0033* (2013.01); *A61B 5/14551* (2013.01);
(Continued)

(58) Field of Classification Search
None
See application file for complete search history.

(56) References Cited

U.S. PATENT DOCUMENTS

2015/0046675 A1* 2/2015 Barry .................... G06F 9/3867
712/7
2016/0260224 A1* 9/2016 Ward .................... G06T 7/0012
(Continued)

FOREIGN PATENT DOCUMENTS

| CN | 106683081 A | 5/2017 |
| CN | 107403201 A * | 11/2017 |
| CN | 107545137 A | 1/2018 |

OTHER PUBLICATIONS

62523691_Specificaiton_2017-06-22 (provisional application of publication 20180369611).*
(Continued)

*Primary Examiner* — Fan Zhang
(74) *Attorney, Agent, or Firm* — Loginov & Associates, PLLC; William A. Loginov

(57) ABSTRACT

A method and system for determining an irradiation dose. The method for determining the irradiation dose includes determining a pixel having a biological feature in a region of interest in a radiotherapy simulated locating image by using a retrospective label; extracting a local radiomics feature based on the pixel having the biological feature, in which the local radiomics feature includes a grayscale histogram intensity, a tumor shape feature, a textural feature, a Laplacian of Gaussian filtering feature, and a wavelet feature; acquiring the local radiomics features to be measured; identifying a positive region having the local radiomics features to be measured based on the local radiomics features; performing three-dimensional reconstruction for the peripheral boundary of the positive region to determine a three-dimensional image.

8 Claims, 13 Drawing Sheets

(51) Int. Cl.
  *A61B 5/1455* (2006.01)
  *A61N 5/06* (2006.01)
  *G06K 9/00* (2006.01)

(52) U.S. Cl.
  CPC .......... *A61B 5/4866* (2013.01); *A61B 5/7275* (2013.01); *A61N 5/06* (2013.01); *G06K 9/0014* (2013.01); *A61N 2005/0627* (2013.01)

(56) References Cited

U.S. PATENT DOCUMENTS

2017/0053090 A1* 2/2017 Viswanath ............. G06N 20/00
2017/0214937 A1* 7/2017 Lin ....................... H04N 19/563
2017/0352157 A1* 12/2017 Madabhushi ......... G06T 7/0012
2018/0369611 A1* 12/2018 Owens ................. A61N 5/1031
2019/0018149 A1* 1/2019 Traub ........................ G01T 1/02

OTHER PUBLICATIONS

Office Action dated Dec. 4, 2019 in corresponding Chinese Application No. 201810480047; 23 pages including English-language translation.

Office Action dated May 6, 2020 in corresponding Chinese Application No. 201810480047; 20 pages including English-language translation.

Gillies et al., " Radiomics: Images Are More Than Pictures, They Are Data", Radiology, vol. 278, No. 2, Feb. 15, 2016 pages.

* cited by examiner

METHOD AND SYSTEM FOR DETERMINING IRRADIATION DOSE

This application claims priority to Chinese application number 201810480047.0, filed May 18, 2018, with a title of METHOD AND SYSTEM FOR DETERMINING IRRADIATION DOSE. The above-mentioned patent application is incorporated herein by reference in its entirety.

TECHNICAL FIELD

The present invention relates to the field of medical radiotherapy, and in particular to a method and system for determining an irradiation dose.

BACKGROUND

Radiotherapy, surgical treatment, and medical chemotherapy are called three major means for oncotherapy. Statistics show that about 65% of patients need to be subjected to radiotherapy during oncotherapy. Some types of cancers (such as early nasopharyngeal carcinoma, lung cancer, breast cancer, and prostate cancer) can be cured by radiotherapy, and the contribution of radiotherapy to tumor curing is 40%.

The general procedure for radiotherapy is as follows:

Step 1, as shown in FIG. 1, is simulated locating, i.e., medically imaging a patient under a condition of a fixed posture.

Step 2, as shown in FIG. 2, is treatment plan design for radiotherapy, i.e., transmitting the image of the previous step to a treatment planning system (TPS) software; simulating an incident angle, a shape, and energy of X ray on this software, and calculating an irradiation dose through the software; simulating the distribution of expose doses of a tumor and organs at risk surrounding it in the patient after radiotherapy implementation; and performing statistical quantitative evaluation in a dose-volume histogram form.

Step 3, plan implementation, i.e., submitting the above radiotherapy plan to a medical linear accelerator for implementation after it is confirmed by both a radiotherapy doctor and a radiological physicist, in which as shown in FIG. 3, before the implementation, firstly the patient is fixed again on a medical linear accelerator treatment table by means of the same fixing device according to the posture used in "Step 1, simulated locating", i.e., "positioning"; then activating a imaging system integrated with the medical linear accelerator, i.e., the CBCT imaging system pointed by a white arrow in FIG. 3, which executes fast imaging of the treatment site of the patient in a time period of about 2 minutes under the circumstance that the patient does not leave the treatment table; subsequently conducting image registration between the image of fast imaging and the patient image used in "Step 2, treatment plan design for radiotherapy", and moving the accelerator treatment table utilizing the posture changes revealed by the registration result, such that the patient's posture is restored to the same posture as that used in "Step 1, simulated locating" and "Step 2, treatment plan design for radiotherapy", as shown in FIG. 4; and finally, calling the radiotherapy plan of the patient to implement radiotherapy for the patient.

For an existing radiotherapy planning method, as described in "Step 2, treatment plan design for radiotherapy" mentioned above, the designing process of the existing radiotherapy plan is formulated under the guidance of anatomical imaging and functional imaging. The anatomical imaging (e.g., CT and MRI) reflects anatomical structures and locations of tumors and normal tissues in the patient, and the functional imaging (e.g., f-MRI, PET, SPECT, etc.) reflects partial biological features in the patient's tumor. By using the anatomical imaging and functional imaging as references, the irradiation field parameters (including shape and intensity of the ray) are adjusted during the pan designing process, so as to simulatedly calculate the dose distribution in the patient and thus complete the plan designing.

As described in "Step 2, treatment plan design for radiotherapy" mentioned above, the formulation process of the existing radiotherapy plan makes reference to the anatomical imaging (e.g., CT and MRI) and the functional imaging (e.g., f-MRI, PET, SPECT, etc.), the limitation of which is reflected in that:

When the radiotherapy plan is formulated under the guidance of the anatomical imaging, the anatomical imaging can only reflect the positions and structures of the tumor and surrounding normal tissues, and cannot reflect biological function information (such as the glucose metabolic level, the hypoxia level, and angiogenesis conditions in the tumor, the magnitude of complications risk in normal tissues, and the like); while for the biological features of the tumor or normal tissues in the human body, on one hand they largely determine the success or failure of radiotherapy (for example, for a hypoxic region in the tumor, the existence of the hypoxic region has direct correlations with distant metastases of the tumor and poor prognosis, and a large number of studies have confirmed that tumor cells in the hypoxic region are resistant to radioactive rays, so that if no high-dose irradiation is conducted, the tumor may not be effectively killed; also for example, as shown in FIG. 5, no volume reduction occurs as seen from the CT anatomical structure of the tumor region indicated by the white arrow, but the CT perfusion functional imaging shows that the blood flow volume is reduced, which means that the tumor-reactive cells have been significantly reduced, and the actual treatment is effective; and also for example, if no targeted protection is performed on a normally functioning lung which is prone to radiation pneumonitis, the patient may have fatal radiation pneumonitis after subjected to the radiotherapy), and on the other hand, there are significant differences among individuals, and there may be huge differences in biological features between two patients with the same type of tumor (for example, after a same irradiation dose of radiotherapy is implemented, the tumor in a radiation-sensitive patient is regressed significantly, while the tumor in a radiation-resistant patient do not change or even proliferate, so that it is essential and necessary to let factors capable of reflecting biological function information to participate in the setting process of the radiotherapy plan.

When the radiotherapy plan is formulated under the guidance of the functional imaging, although the functional imaging reflects specific biological function information (such as glucose metabolism conditions, hypoxia conditions, and angiogenesis conditions in the tumor, and angiogenesis conditions in the tumor, the magnitude of complications risk in normal tissues, and the like), it has many limitations, including:

(1) The location and anatomical information cannot be accurately reflected. The f-MRI, PET and SPECT images, while reflecting the biological functions of some regions, cannot accurately reflect the accurate anatomical location of the region, and the functional region can be directed to the corresponding anatomical position only through image fusion of these images with an anatomical image (i.e., overlaying of the two kinds of images), and as shown in FIGS. 6 to 8, the highlighted region in FIG. 8 is a region with a specific biological function, such as a tumor region having glucose hypermetabolism or a hypoxic tumor region; but such a "directed to" is often less accurate, as its accuracy is completely dependent on the image fusion algorithm, and images of different modalities often have problems such as distortion and inconsistent scale, and thus no truly one-to-one correspondence can be achieved.

(2) The cost of functional imaging is very expensive, ranging from more than 1,000 yuan per time (SPECT) to nearly 10,000 yuan per time (PET, a non-medical insurance reimbursement item, completely at people's own expense), so that it is difficult to carry out among most patients and cannot benefit more patients.

(3) Functional imaging such as PET and SPECT require injecting radioisotopes into the patient's body, which brings additional radiation to the patient, and in turn brings the limitation that the total number of functional imaging scans subjected by the same patient during the treatment course should not be too many (usually the patient only subjected to the functional imaging scan once before the radiotherapy begins, and at most subjected to the functional imaging scan once again after the radiotherapy, that is the patient is subjected to the functional imaging scans for 2 times before and after in total.

(4) One type of functional imaging can only reveal one biological function feature. For example, 18F-FETNIM PET can reveal the hypoxic region in the tumor, and thus promote that it is appropriate to increase the irradiation dose in this region during the treatment planning process, but 18F-FETNIM PET can only reflect such a feature of "tumor hypoxia" and cannot explain other biological function features such as angiogenesis, glucose metabolism in the tumor, and currently there is no tracer agent that can display multiple functional features at the same time after injected into the human body.

In view of the above existed problems, a method for identifying where is tumor and where is non-tumor by extracting local radiomics features is studied abroad. For the region which is identified as a tumor, a higher irradiation dose is given in the radiotherapy course, and for the region which is identified as non-tumor, a relatively lower prophylactic irradiation dose is given. However, since the biological features at different locations in tumor region are inhomogeneous, if homogeneous irradiation doses are given to the tumor region and the non-tumor region, the tumor cells cannot be completely killed in the tumor region. Therefore, being unable to give respective irradiation doses to tumors with different biological features in the tumor region may affect the therapeutic effect of radiotherapy.

SUMMARY

The object of the present invention is to provide a method and system for determining an irradiation dose, so as to solve the problem in the prior art that irradiation doses cannot be given correspondingly to tumors respecting to different biological features both in the tumor region and in the organs at risk, which affects the therapeutic effect and side-effects of radiotherapy.

A method for determining an irradiation dose, including:
determining a pixel having a biological feature in a region of interest in a radiotherapy simulated locating image by using a retrospective label, where the radiotherapy simulated locating image includes computed tomography imaging, nuclear magnetic resonance imaging, and positron emission tomography imaging, and the biological feature includes the glucose metabolism conditions, hypoxic regions, oxygen-enriched regions, angiogenesis conditions in the tumor, and the magnitude of complications risk in normal tissues;
extracting the local radiomics feature based on the pixel having the biological feature, where the local radiomics feature includes a grayscale histogram intensity, a tumor shape feature, a textural feature, a Laplacian of Gaussian (LoG) filtering feature, and a wavelet feature;
acquiring the local radiomics feature to be measured;
identifying a positive region having the local radiomics feature to be measured based on the local radiomics feature;
performing three-dimensional reconstruction for the peripheral boundary of the positive region to determine a three-dimensional image, where the three-dimensional image is a three-dimensional image displaying the biological features; and
determining irradiation doses at different locations in different regions based on the three-dimensional image.

Alternatively, the extracting the local radiomics feature based on the pixel having the biological feature specifically includes:
extracting local radiomics features from pixels having the biological features pixel by pixel through a per-pixel method by adopting a grayscale histogram feature extraction method, a textural feature extraction method, a LoG filtering feature extraction method, and a wavelet feature extraction method.

Alternatively, the identifying a positive region having the local radiomics feature to be measured based on the local radiomics feature specifically includes:
screening the local radiomics features to determine an optimal feature subset;
establishing a supervised machine learning model based on the optimal feature subset; and
identifying a positive region having the local radiomics features to be measured based on the supervised machine learning model.

Alternatively, the screening the local radiomics features to determine an optimal feature subset specifically includes:
screening the local radiomics features through a feature selection method so as to determine an optimal feature subset, where the feature selection method includes Minimum Redundancy-Maximum Relevance.

Alternatively, the determining irradiation doses at different locations in different regions based on the three-dimensional image specifically includes:
determining an irradiation dose parameter based on the three-dimensional image, where the irradiation dose parameter includes an incident angle, an intensity, and a shape; and
determining irradiation doses at different locations in different regions based on the irradiation dose parameter.

A system for determining an irradiation dose, including:
a pixel determining module for determining a pixel having a biological feature in a region of interest in a radiotherapy simulated locating image by using a retrospective label, where the radiotherapy simulated locating image includes computed tomography imaging, nuclear magnetic resonance imaging, and positron emission tomography imaging, and the biological feature includes the glucose metabolism conditions, hypoxic regions, oxygen-enriched regions, angiogenesis conditions in the tumor, and the magnitude of complications risk in normal tissues;
a local radiomics feature extraction module for extracting a local radiomics feature based on the pixel having the biological feature, where the local radiomics feature includes a grayscale histogram intensity, a tumor shape feature, a textural feature, a LoG filtering feature, and a wavelet feature;

an acquisition module for acquiring the local radiomics features to be measured;

a positive-region identification module for identifying a positive region having the local radiomics features to be measured based on the local radiomics features;

a three-dimensional reconstruction module for performing three-dimensional reconstruction for the peripheral boundary of the positive region to determine a three-dimensional image, where the three-dimensional image is a three-dimensional image displaying the biological features; and an irradiation dose determination module for determining irradiation doses at different locations in different regions based on the three-dimensional image.

Alternatively, the local radiomics feature extraction module specifically includes:

a local radiomics feature extraction unit for extracting local radiomics features from pixels having the biological features pixel by pixel through a per-pixel method by adopting a grayscale histogram feature extraction method, a textural feature extraction method, a LoG filtering feature extraction method, and a wavelet feature extraction method.

Alternatively, the positive-region identification module specifically includes:

a screening unit, for screening the local radiomics features to determine an optimal feature subset;

a model establishing module for establishing a supervised machine learning model based on the optimal feature subset, and a positive-region identification unit for identifying a positive region having the local radiomics features to be measured based on the supervised machine learning model.

Alternatively, the screening unit specifically includes:

a screening subunit for screening the local radiomics features through a feature selection method so as to determine an optimal feature subset, where the feature selection method includes Minimum Redundancy-Maximum Relevance.

Alternatively, the irradiation dose determination module specifically includes:

an irradiation dose parameter determination unit for determining an irradiation dose parameter based on the three-dimensional image, where the irradiation dose parameter includes an incident angle, an intensity, and a shape; and an irradiation dose determination unit for determining irradiation doses at different locations in different regions based on the irradiation dose parameter.

According to a specific embodiment provided by the present invention, the present invention discloses the following technical effects: the present invention provides a method and system for determining an irradiation dose, including: determining a pixel of a biological feature; extracting a local radiomics feature according to the pixel; determining the positive region having the local radiomics feature to be measured based on the local radiomics feature; and in turn establishing a three-dimensional image capable of displaying the biological features at different locations in different regions, so that respective irradiation doses at different locations in different regions can be determined based on the three-dimensional image. Therefore, even when the tumors are in the same the tumor region, different irradiation doses can be given to different tumors based on differences in the biological features in the tumor region, so that the irradiation dose can be given based on the actual tumor condition, thereby improving the therapeutic effect of radiotherapy.

BRIEF DESCRIPTION OF DRAWINGS

To describe the technical solutions in the embodiments of the present invention or in the prior art more clearly, the following briefly describes the accompanying drawings required for describing the embodiments. Apparently, the accompanying drawings in the following description show some embodiments of the present invention, and a person of ordinary skill in the art may still derive other drawings from these accompanying drawings without creative efforts.

DETAILED DESCRIPTION

Figure 1:
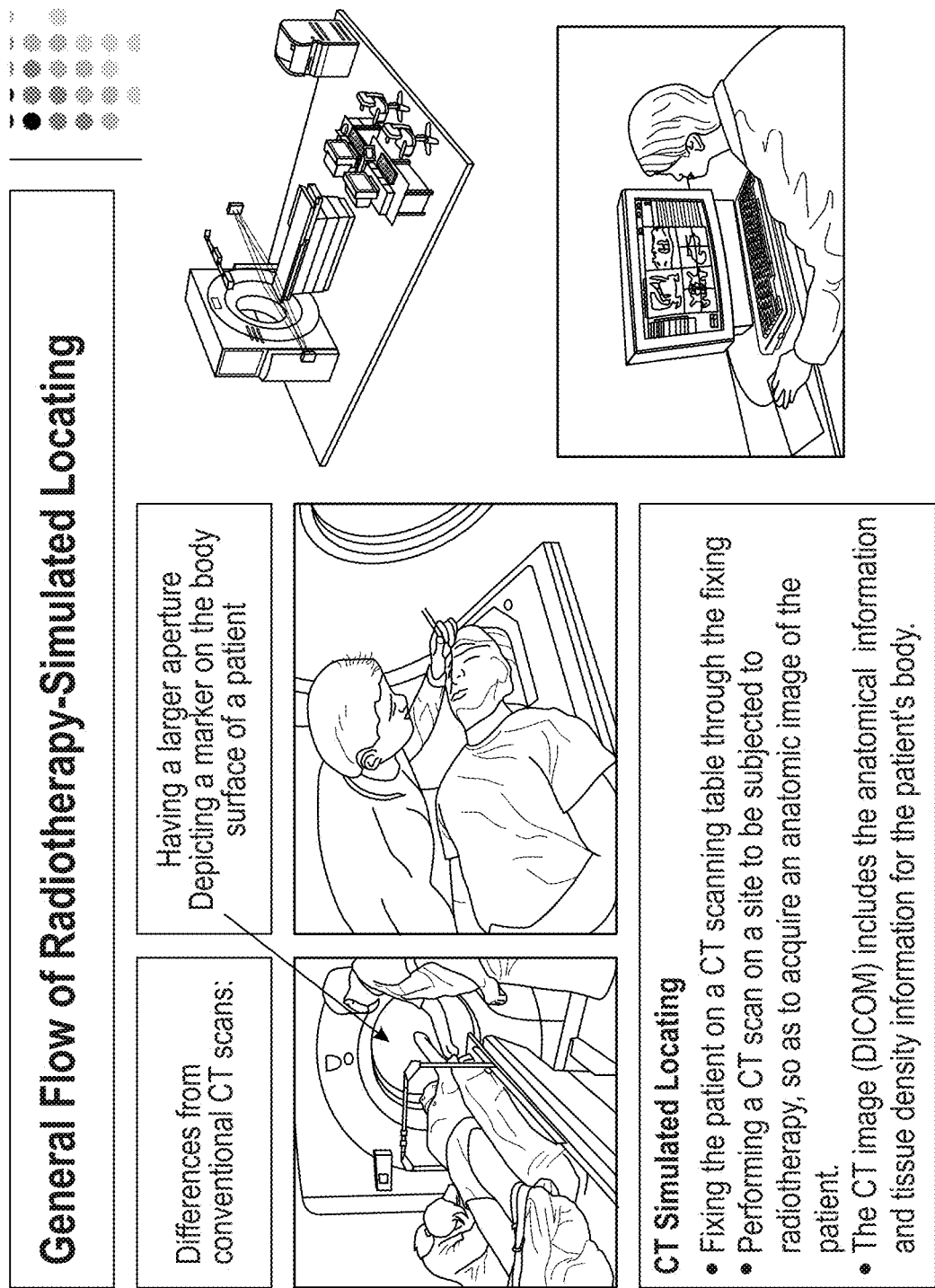
FIG. 1 is a flowchart for simulated locating provided by the present invention.
Figure 2:
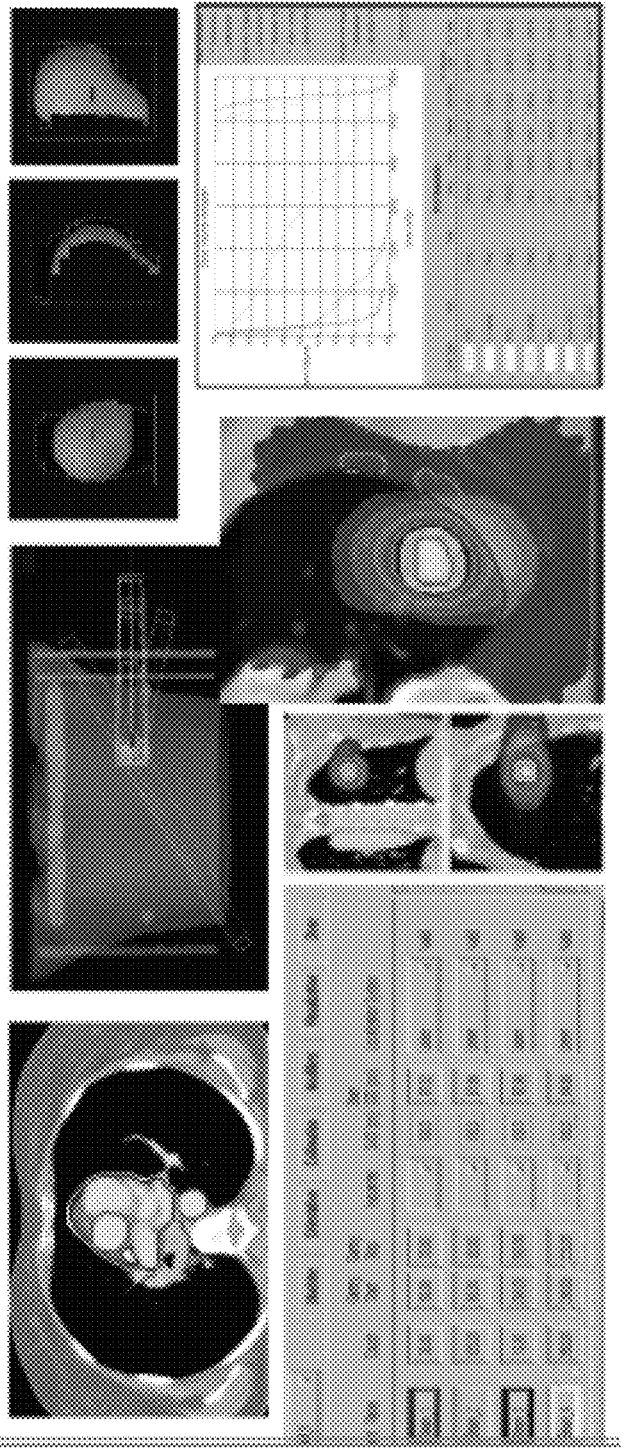
FIG. 2 is a flowchart for formulating a radiotherapy plan provided by the present invention.
Figure 3:
FIG. 3 is an actual diagram when cone-beam CT is scanning during image guided radiotherapy as provided by the present invention.
Figure 4:
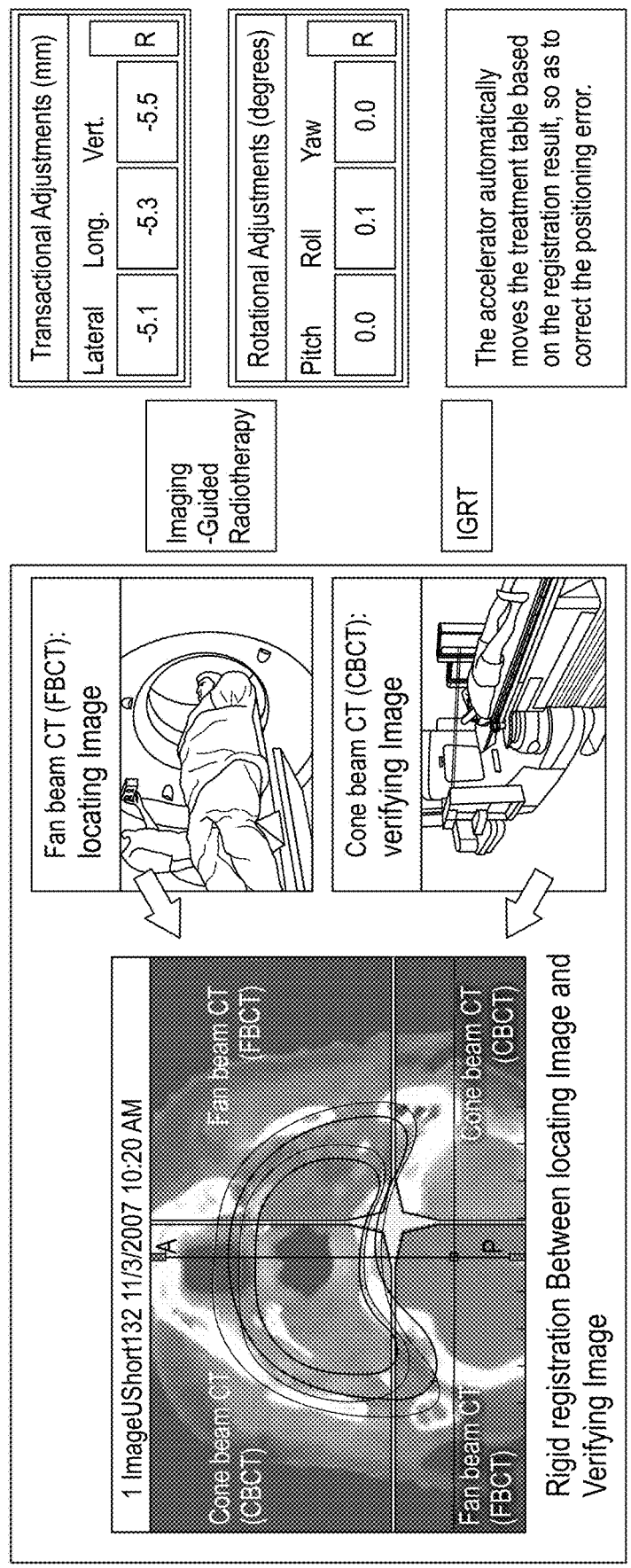
FIG. 4 is an actual diagram when cone-beam CT and planning fan beam KVCT were registered to verify the patient position before the radiotherapy plan is formulated as provided by the present invention.
Figure 5:
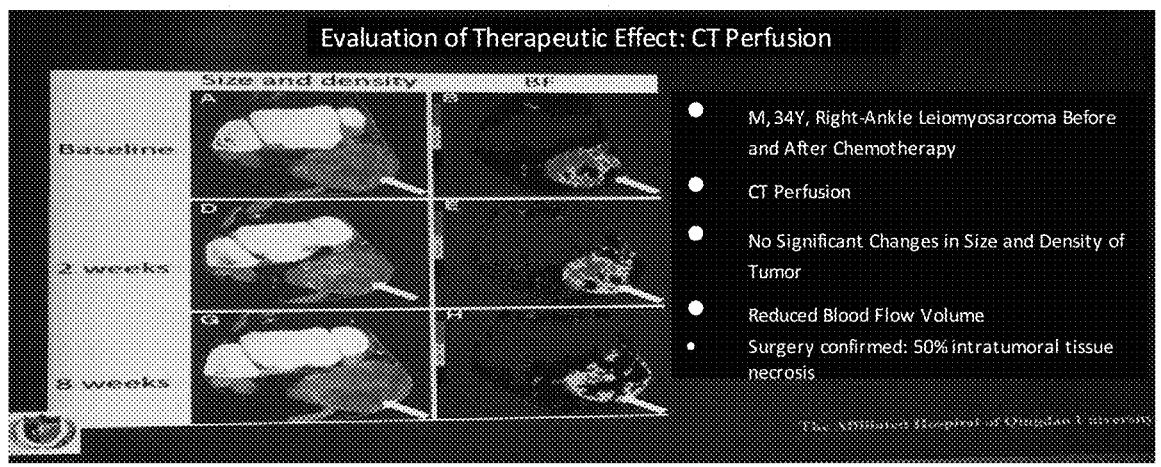
FIG. 5 is a schematic CT perfusion diagram provided by the present invention, which indicated that biological function images present more important information than anatomy images at determining irradiation dose.
Figure 6:
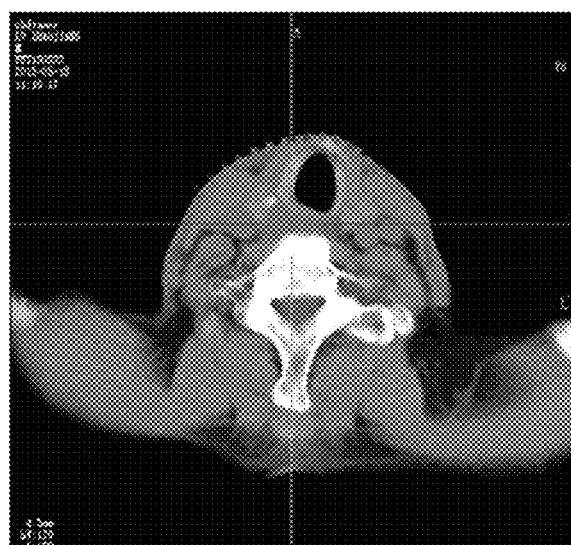
FIG. 6 is a computed tomography image provided by the present invention.
Figure 7:
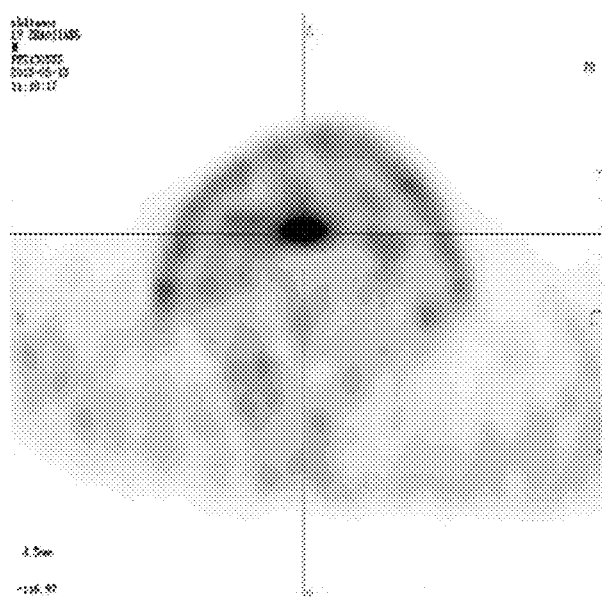
FIG. 7 is a corresponding positron emission tomography image with FIG. 6 provided by the present invention.
Figure 8:
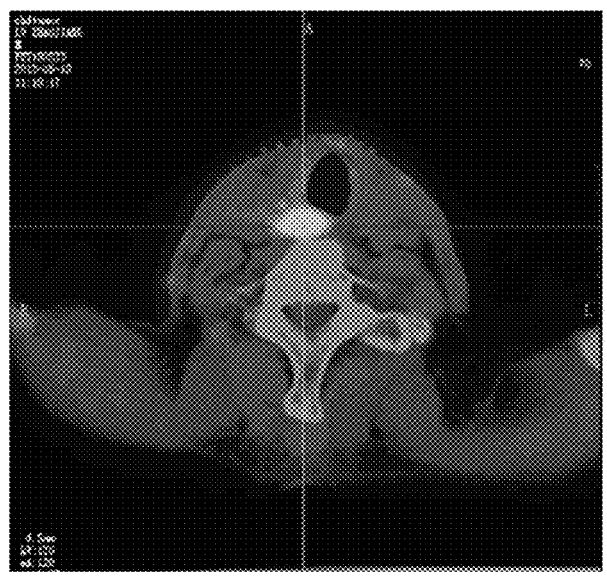
FIG. 8 is a schematic image diagram after fusion between a computed tomography image and a positron emission tomography image, as provided by the present invention.

The following clearly and completely describes the technical solutions in the embodiments of the present invention with reference to the accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

The object of the present invention is to provide a method and system for determining an irradiation dose, which can give the irradiation dose based on the actual tumor condition and thus improve the therapeutic effect of radiotherapy.

In order to make the above objects, features, and advantages of the present invention more apparent, the present invention will be further described in detail in connection with the accompanying drawings and the detailed description.

Radiomics (also translated as "image-omics", but the expression "radiomics" is more prevalent in China, and in the subject categories of National Natural Science Foundation of China (NSFC), a new third-level subject called "radiomics and artificial intelligence" has been recently introduced, and thus the expression "radiomics" is followed) is an emerging tumor diagnosis and aided detection technique, which particularly has been rapidly developed in recent decades. Radiomics refers to applying a large number of automated data feature extraction algorithms to convert the image data of a region of interest into data of a first or higher order, and further improving the accuracy of clinical diagnosis and the predictive value of prognosis by performing data mining and analyzing the deep relationships in the data.

Studies have confirmed that there are significant correlations between the local radiomics feature indexes extracted from images of CT, MRI, and PET and the biological features of the tumor itself and the clinical therapeutic effect on the tumor. For example: (1) some local radiomics feature indexes extracted from the tumor region are related to the internal heterogeneity of the tumor, pointing to glucose metabolism conditions, whether it is hypoxia or oxygen-rich, and whether there is angiogenesis in different regions inside the tumor; (2) some local radiomics feature indexes extracted from the tumor region are related to response sensitivity of the tumor after it is subjected to radiotherapy or chemotherapy, and these indexes can be used to predict the therapeutic effect of radiotherapy and chemotherapy; (3) some local radiomics feature indexes extracted from the lung tissue region are related to the possibility of radiation pneumonitis in a patient after he/she is subjected to radiotherapy, which can be used before treatment for predicting the risk of complications in the patient after he/she is subjected to radiotherapy; and (4) local radiomics features extracted from a tumor region reflected by a CT image of a patient with oropharyngeal cancer are correlated with occurrence of distant metastases in the patient, which can be used before treatment for predicting the risk of distant metastases in the patient.

All of the above studies have been published on top journals in the industry field and have been widely accepted in the industry.

However, all of existing studies have focused on revealing the correlations between different feature indexes and different clinical manifestations, and few studies have explored the use of these indexes for guiding the formulation of a radiotherapy plan. Relevant studies have shown that, some local radiomics feature indexes for prostate regions of a patient with prostate cancer are extracted from a MRI image to identify tumor cell growth regions in the prostate, then these regions are overlapped on a corresponding CT image through image registration and are identified as targeted tumor regions, and subsequently a radiotherapy plan for the targeted tumor regions is formulated on the CT image; however, although the hypoxic region and the oxygen-enriched region both are tumor regions, the hypoxic region in the tumor needs to be subjected to a higher irradiation dose than that for the tumor in the oxygen-enriched region to kill the cell, and since the biological features at different locations in different regions are different, if the same irradiation dose is given to different tumors or the same tumor in different regions according to the radiotherapy plan of the prior art, the effect of radiotherapy is extremely poor.

Figure 9:
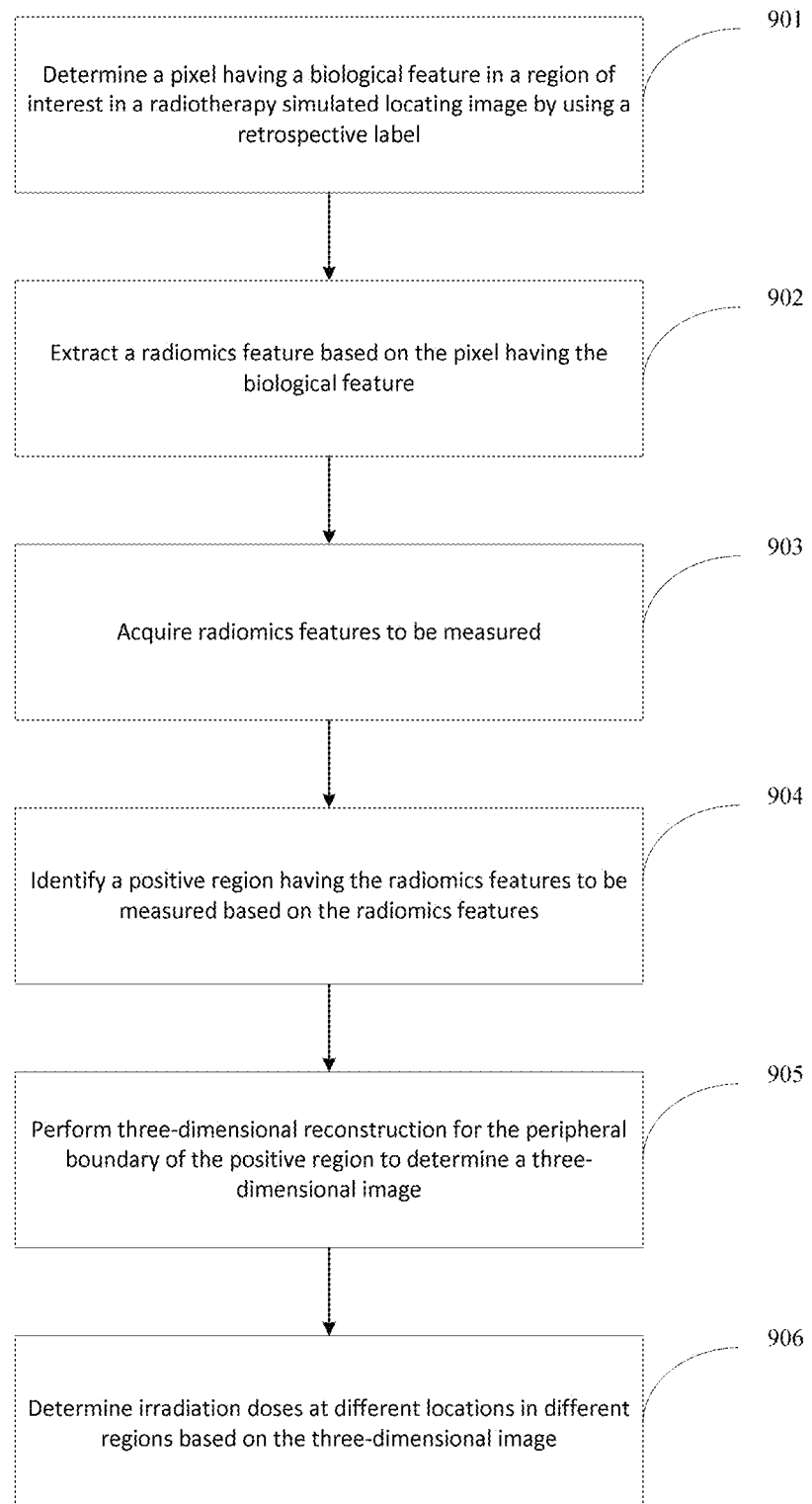
FIG. 9 is a flow chart of an irradiation dose determining method provided by the present invention.

FIG. 9 is a flowchart of a method for determining an irradiation dose, as provided by the present invention. As shown in FIG. 9, the method for determining the irradiation dose includes:

Step 901: determining a pixel having a biological feature in a region of interest in a radiotherapy simulated locating image by using a retrospective label; in which the radiotherapy simulated locating image includes computed tomography imaging, nuclear magnetic resonance imaging, and positron emission tomography imaging; and the biological feature includes the glucose metabolism conditions, hypoxic regions, oxygen-enriched regions, angiogenesis conditions in the tumor, and the magnitude of complications risk in normal tissues.

Figure 10:
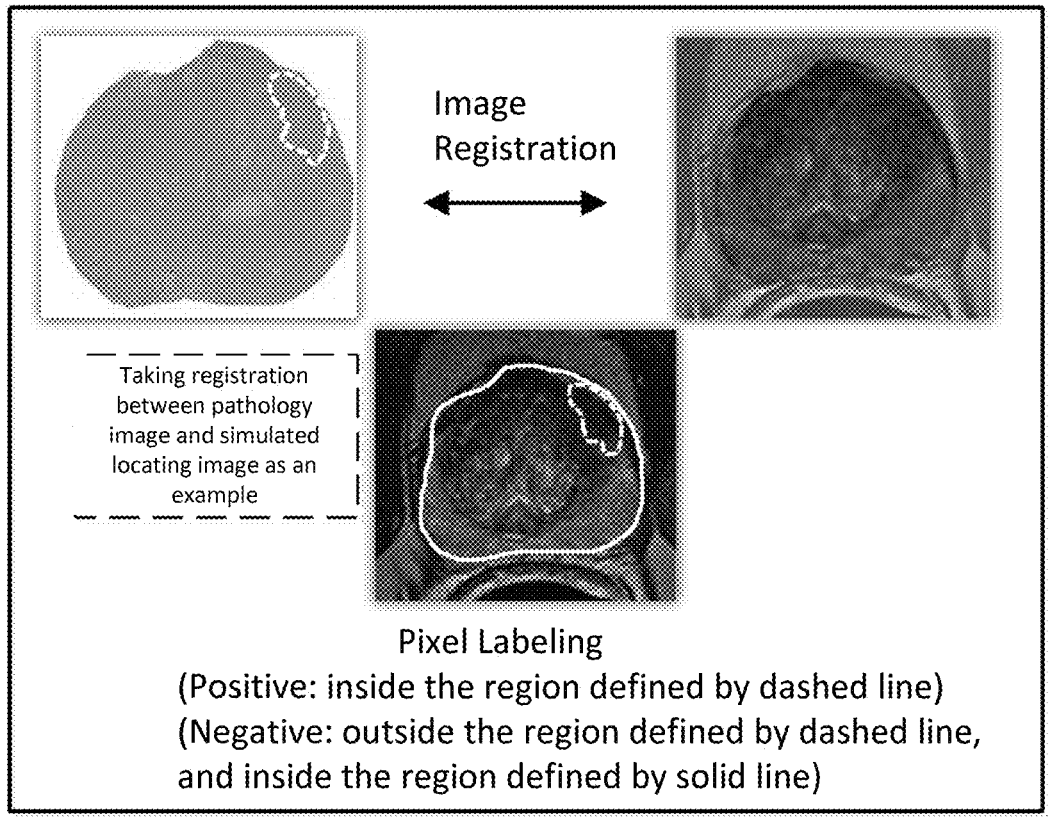
FIG. 10 is a schematic diagram of a positive region label provided by the present invention.

As shown in FIG. 10, pixels being biological-feature positive in a region of interest of the radiotherapy simulated locating image (e.g., computed tomography imaging, nuclear magnetic resonance imaging, positron emission tomography imaging, cone beam CT, single photon emission computerized tomography, megavoltage CT, electronic portal imaging system, barium meal fluoroscopy image, and the like) for patients entered a training set and a validation set are retrospectively labeled. That is, through retrospective analysis, an image registration between the patient's pathological section images, functional images (for example, 18F-FETNIM PET/CT can non-invasively display the hypoxic region in a tumor) or other images reflecting biological features of the region of interest (e.g., a region of lung tissue in which radioactive pneumonitis occurs), and the radiotherapy simulated locating image is conducted, and then based on whether pixels (pixels, P) in the pathological section images, functional images or other images reflecting biological features of the region of interest have a biological feature of interest, the corresponding pixels in the region of interest (ROI) of the radiotherapy simulated locating image are labeled (Positive pixel is labeled with 1, and the negative pixel is labeled with 0).

All pixels in a ROI of a certain region of interest are defined as a set P={plable 1, plabel 2, . . . , plabel n}, where n represents the number of pixels, and label represents a mark of a pixel (1 refers to positive, and 0 refers to negative).

Step 902: extracting a local radiomics feature based on the pixel having the biological feature; in which the local radiomics feature includes a grayscale histogram intensity, a tumor shape feature, a textural feature, a Laplacian of Gaussian (LoG) filtering feature, and a wavelet feature.

Figure 11:
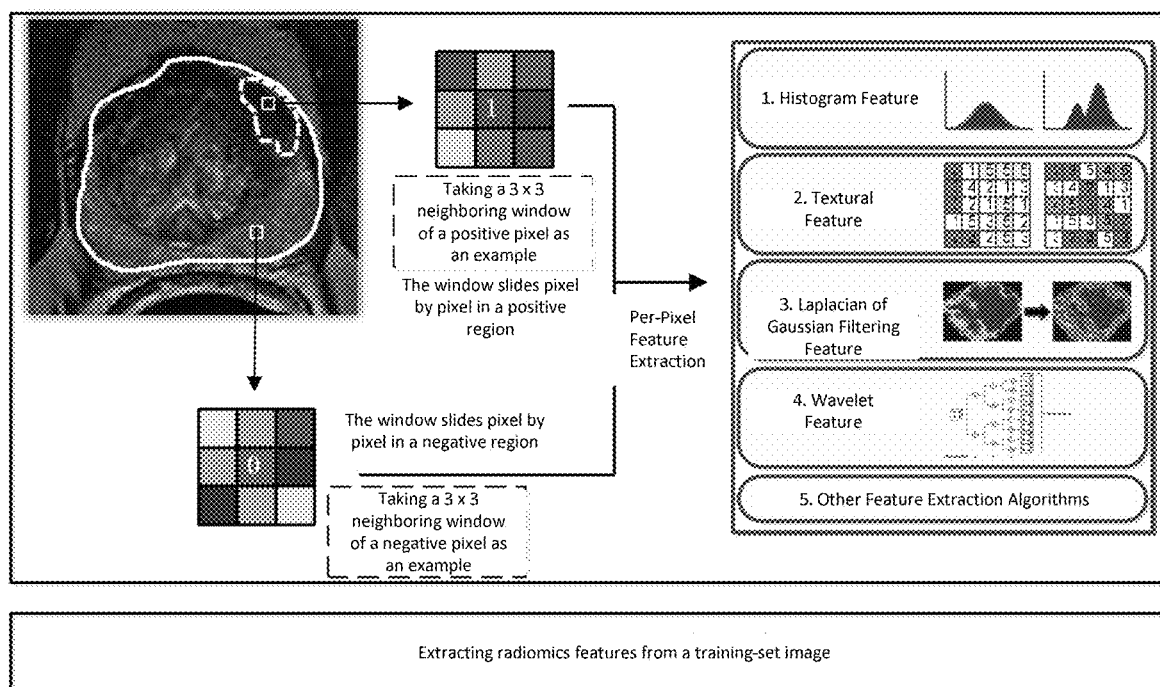
FIG. 11 is a flow chart for extracting a local radiomics feature, as provided by the present invention.

As shown in FIG. 11, local radiomics features of positive and negative pixels in each region of interest ROI (e.g., the targeted tumor region) of the radiotherapy simulated locating image are extracted.

(1) Local radiomics feature extraction algorithms include but not limited to grayscale histogram feature extraction algorithm, the number of features extracted by it being labeled as N1;

textural feature extraction algorithm, the number of features extracted by it being labeled as N2;

Laplacian of Gaussian (LoG) filtering feature extraction algorithm, the number of features extracted by it being labeled as N3;

wavelet decomposition feature extraction algorithm, the number of features extracted by it being labeled as N4; and Other extraction algorithms for feature extraction, the number of features extracted by them being labeled as N5;

Therefore, the total number of features is $N=N1+N2+N3+N4+N5$; and the feature value is represented by $f_j(p)$, in which $p \in P$, and $j \in \{1, \ldots, N\}$).

(2) Pixel-Based Local feature Extraction. All of the pixels in each ROI of the radiotherapy simulated locating image are traversed, and the local radiomics feature values of the surrounding δ×δ×δ (for three-dimensional images) or δ×δ (for two-dimensional images) neighboring windows are calculated by using each pixel as the center, in which δ is an odd number greater than or equal to 3, and the δ value is taken as 3, 5, 7, and 9 respectively each time for the calculation of local features, such a selection in the subsequent modeling and verification steps enabling recognition of a δ value with the optimum accuracy. For pixels on the boundary, symmetric filling is adopted, and the value of the fill pixel is a mirror reflection of the boundary pixel.

(3) Through step (2) Pixel-Based Local feature Extraction, a 1×N dimension feature vector Flabel i={$f_1$(plabel i), $f_2$(plabel i), ..., $f_j$(plabel i)}, j∈{1, ..., N}, i∈{1, ..., n}, label∈{1,0} (i.e., for the pixel plabel i, N feature values can be extracted, which are $f_1(p_i)$, $f_2(p_i)$, ..., $f_j(p_i)$ respectively, and are marked as a vector Flabel i) can be obtained for each pixel (p∈P) at a specific δ value. Therefore, for all pixels in the ROI, the feature set is $\boldsymbol{F}$={Flabel i, ..., Flabel n}, label∈{1,0}. Each pixel (label=1/0) serves as one sample with N-dimensional local radiomics features.

Step 903: acquiring local radiomics features to be measured.

Step 904: identifying a positive region having the local radiomics features to be measured based on the local radiomics features.

Figure 12:
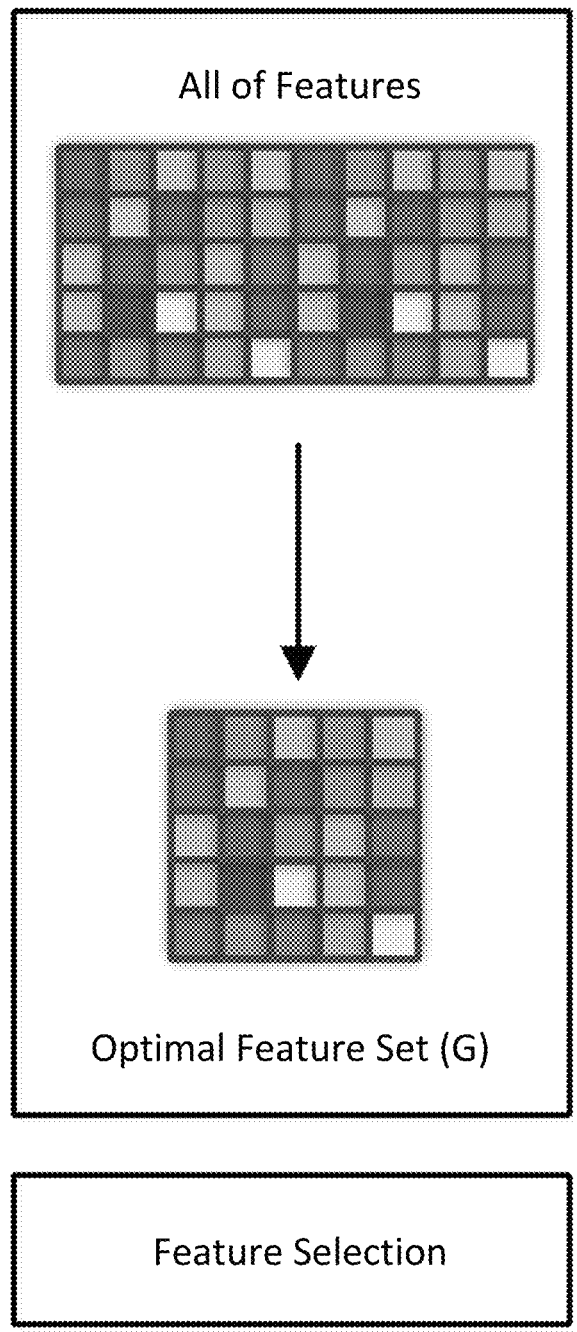
FIG. 12 is a flowchart for selecting an optimal feature subset, as provided by the present invention.

The step 904 specifically includes:

as shown in FIG. 12, the local radiomics features are screened to determine the optimal feature subset. Based on the training set, through a relevant feature selection algorithm (including but not limited to Minimum Redundancy-Maximum Relevance (mRMR)), a feature parameter having the maximum relevance with the classification labels and the minimum redundancy between the features is screened out for the next step of establishing a prediction model. Through this step, the optimal feature subset G={$f_1(p)$, $f_2(p)$, ..., $f_k(p)$} is obtained. Each labeled pixel (label=1/0) and its local radiomics features serve as one sample to participate in feature selection, and both positive and negative pixels participate in this process. The screened-out optimal feature subset is the same set.

Figure 13:
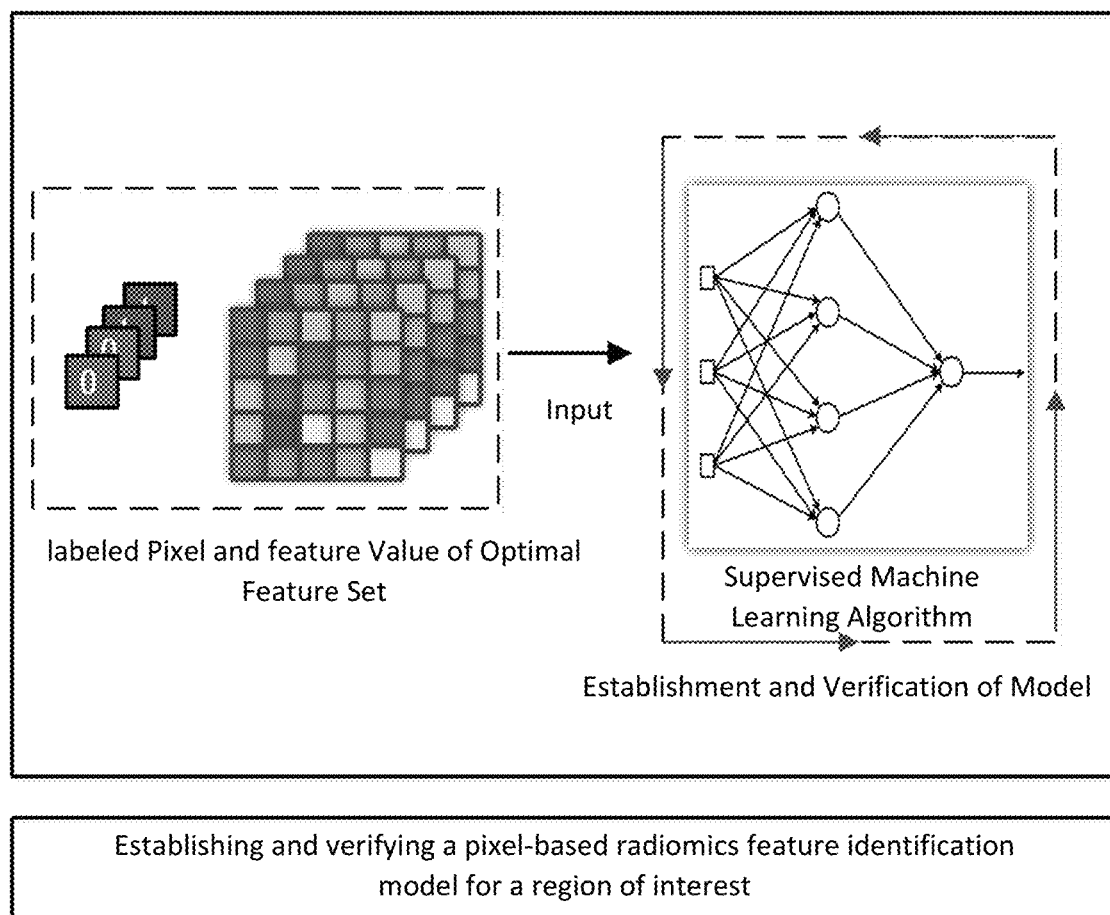
FIG. 13 is a flow chart for establishing a supervised machine learning recognition model, as provided by the present invention.

As shown in FIG. 13, a supervised machine learning model is established based on the optimal feature subset. (1) Modeling: based on a training set, the radiomics features described in the optimal feature set G of a labeled pixel (label=1/0) are input into a supervised machine learning algorithm, so as to establish a supervised machine learning recognition model. Each labeled pixel (label=1/0) participates in the model establishment as one sample.

(2) Verification: the identification accuracy of the model is verified based on the data of a verification set, and a feature extraction window (δopt) that makes the identification accuracy optimal is selected.

Figure 14:
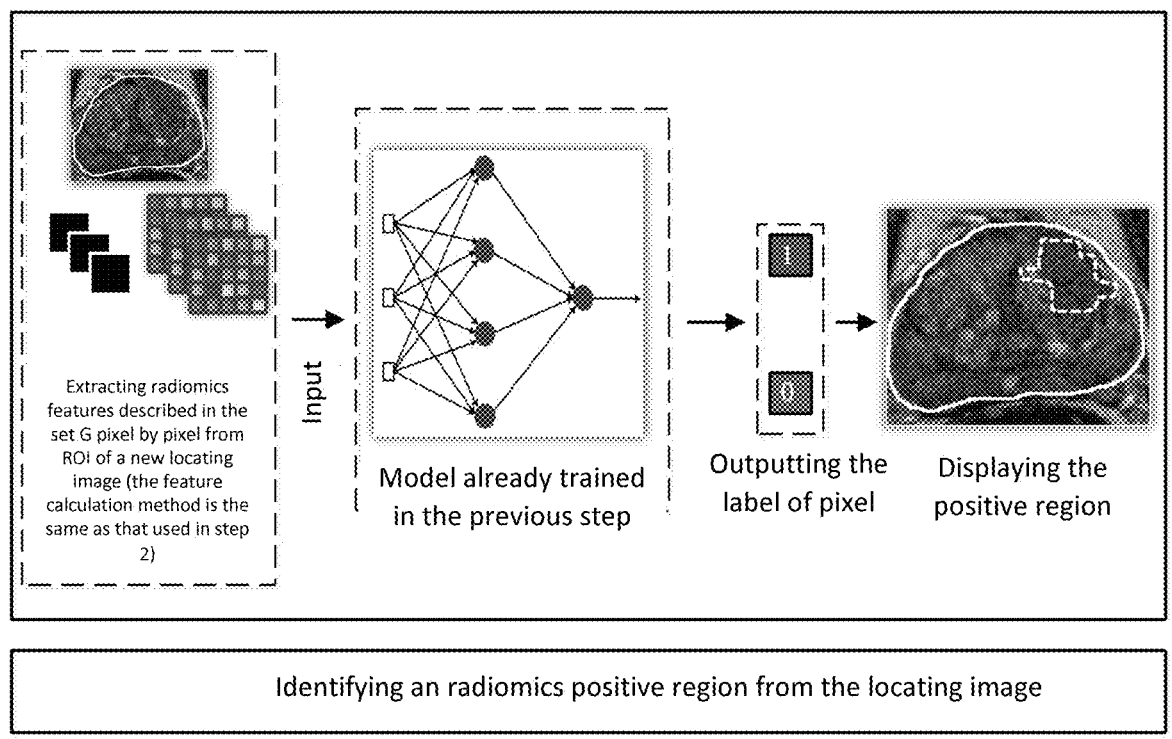
FIG. 14 is a flowchart for identifying a positive region having the local radiomics feature to be measured, as provided by the present invention.

As shown in FIG. 14, a positive region having the local radiomics features to be measured is identified based on the supervised machine learning model. For a new locating image for which a local radiomics feature-guided radiotherapy plan is to be formulated, the local radiomics features described in the set G are extracted pixel by pixel through a neighboring window having the size of $δ_{opt}$; and the feature parameters of each pixel are input into the identification model established in step 4, and this model will output the biological-function expression label of the current pixel (positive: 1, and negative 0). The pixels being positive for the same biological function are labeled with a unified color, i.e., displaying a biological-function positive region on each tomography image.

Step 905: performing three-dimensional reconstruction for the peripheral boundary of the positive region to determine a three-dimensional image; in which the three-dimensional image is a three-dimensional image displaying the biological features.

Three-dimensional reconstruction for the peripheral boundary of the positive region identified in step 904 is performed, and the stereostructure of the biological functional region is reconstructed in the imaging space of the planning system to determine the three-dimensional image.

Step 906: determining irradiation doses at different locations in different regions based on the three-dimensional image.

On the basis of the biological features reconstructed from the three-dimensional image, irradiation field parameters including an incident angle, an intensity and a shape are set, and constraint conditions of dose-volume or biological factors such as complication probability of normal tissues and tumor control probability are given to the region, so as to conduct plan designing and goal optimization.

The present invention predicts changes that may occur after the patient is subjected to radiotherapy (including changes in the tumor such as regressing, being resistant and remained, and increasing, and including possible complications in a normal tissue) through textural features of a local anatomic region of human body (which may be a tumor region, or a normal tissue region) extracted from medical images (the medical images include computed tomography imaging, nuclear magnetic resonance imaging, positron emission tomography imaging, cone beam CT, single photon emission computerized tomography, megavoltage CT, electronic portal imaging system, and barium meal fluoroscopy image, but are not limited to these images, in the future there may be other images for setting the radiotherapy plan, and all of these images are applicable to the technology), and thus uses this as a guidance to formulate a radiotherapy plan specifically for the patient, thereby achieving targeted and individualized precise radiotherapy and improving the therapeutic benefits for the patient.

Figure 15:
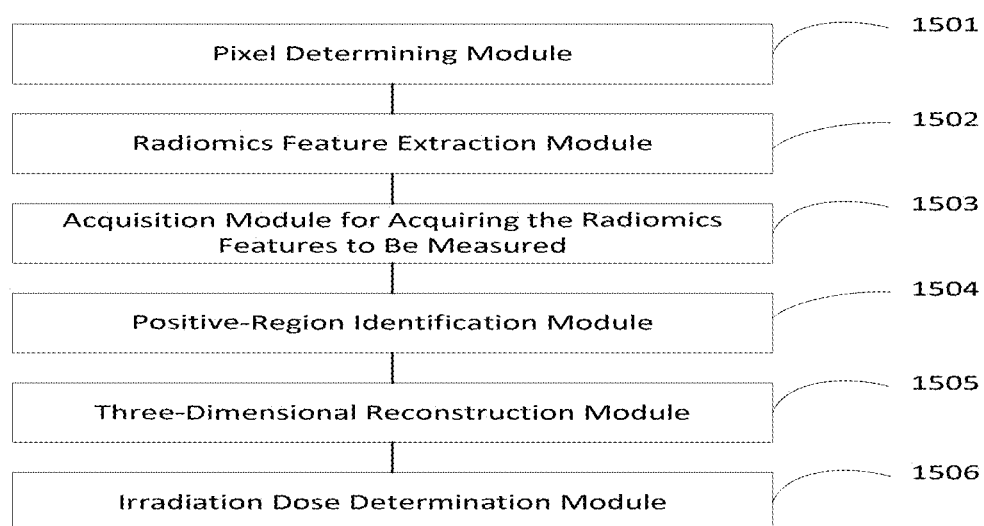
FIG. 15 is a structural diagram of an irradiation dose determining system provided by the present invention.

FIG. 15 is a structural diagram of an irradiation dose determining system provided by the present invention. As shown in FIG. 15, an irradiation dose determining system includes:

a pixel determining module 1501 for determining a pixel having a biological feature in a region of interest in a radiotherapy simulated locating image by using a retrospective label, in which the radiotherapy simulated locating image includes computed tomography imaging, nuclear magnetic resonance imaging, and positron emission tomography imaging, and the biological feature includes the glucose metabolism conditions, hypoxic regions, oxygen-enriched regions, angiogenesis conditions in the tumor, and the magnitude of complications risk in normal tissues;

a local radiomics feature extraction module 1502 for extracting a local radiomics feature based on the pixel having the biological feature, in which the local radiomics feature includes a grayscale histogram intensity, a tumor shape feature, a textural feature, a LoG filtering feature, and a wavelet feature, the local radiomics feature extraction module 1502 specifically includes: a local radiomics feature extraction unit for extracting local radiomics features from pixels having the biological features pixel by pixel through a per-pixel method by adopting a grayscale histogram feature extraction method, a textural feature extraction method, a LoG filtering feature extraction method, and a wavelet feature extraction method;

an acquisition module 1503 for acquiring the local radiomics features to be measured;

a positive-region identification module 1504 for identifying a positive region having the local radiomics features to be measured based on the local radiomics features, in which the positive-region identification module 1504 specifically includes:

a screening unit for screening the local radiomics features to determine an optimal feature subset, a model establishing module for establishing a supervised machine learning model based on the optimal feature subset, and a positive-region identification unit for identifying a positive region having the local radiomics features to be measured based on the supervised machine learning model, and the screening unit specifically includes: a screening subunit for screening the local radiomics features through a feature selection method so as to determine an optimal feature subset, in which the feature selection method includes Minimum Redundancy-Maximum Relevance (mRMR);

a three-dimensional reconstruction module 1505 for performing three-dimensional reconstruction for the peripheral boundary of the positive region to determine a three-dimensional image, in which the three-dimensional image is a three-dimensional image displaying the biological features; and an irradiation dose determination module 1506 for determining irradiation doses at different locations in different regions based on the three-dimensional image, in which the irradiation dose determination module 1506 specifically includes: an irradiation dose parameter determination unit for determining an irradiation dose parameter based on the three-dimensional image, in which the irradiation dose parameter includes an incident angle, an intensity, and a shape; and an irradiation dose determination unit for determining irradiation doses at different locations in different regions based on the irradiation dose parameter.

Existing studies only identify where is tumor and where is non-tumor in a prostate region through a local radiomics feature extraction technique. For the region which is identified as a tumor, a higher irradiation dose is given in the plan designing process, and for the region which is identified as non-tumor, a relatively lower prophylactic irradiation dose is given.

However, the present invention provides a method and system for determining an irradiation dose. On one hand, it can not only identify whether it is a tumor region, but also identify biological differences in the tumor region, in which for example: although the hypoxic region and the oxygen-enriched region both are tumor regions, the hypoxic region in the tumor needs to be subjected to a higher irradiation dose than that for the tumor in the oxygen-enriched region to kill the cell, and thus the present invention is a method and system for determining an irradiation dose based on comprehensively identified local radiomics features of a tumor; and on the other hand, the present invention can not only identify a tumor, but also identify biological features of a normal tissue region, in which for example: local radiomics features have been extracted from the lung tissue before plan designing for a thoracic tumor, and thus the microscopic structure changes in the lung tissue can be found in the circumstance that these changes cannot been seen by human eyes, so as to timely prompt a doctor and a physicist to specifically reduce the exposure dose of lung tissue in a certain region during plan designing, thereby achieving a truly "built-to-suit" planning method and improving the therapeutic effect of radiotherapy.

Each embodiment of the present specification is described in a progressive manner, each embodiment focuses on the difference from other embodiments, and the same and similar parts between the embodiments may refer to each other. For a system disclosed in the embodiments, since it corresponds to the method disclosed in the embodiments, the description is relatively simple, and reference can be made to the method description.

Several examples are used for illustration of the principles and implementation methods of the present invention. The description of the embodiments is used to help illustrate the method and its core principles of the present invention. In addition, those skilled in the art can make various modifications in terms of specific embodiments and scope of application in accordance with the teachings of the present invention. In conclusion, the content of this specification shall not be construed as a limitation to the invention.

What is claimed is:

1. A method for determining an irradiation dose, comprising:

determining a pixel having a biological feature in a region of interest in a radiotherapy simulated locating image by using a retrospective label, wherein the radiotherapy simulated locating image includes computed tomography imaging, nuclear magnetic resonance imaging, and positron emission tomography imaging, and the biological feature comprises the glucose metabolism level, oxygen content level, angiogenesis conditions in the tumor, and the magnitude of complications risk in normal tissues; wherein the determining a pixel having a biological feature in a region of interest in a radiotherapy simulated locating image by using a retrospective label comprises: carrying out an image registration between images reflecting biological features of the region of interest and the radiotherapy simulated locating image by retrospective analysis, and then labeling corresponding pixels in the region of interest of the radiotherapy simulated locating image base on whether pixels in the images reflecting biological features of the region of interest have a biological feature of interest, wherein labeling positive pixel with 1 while labeling negative pixel with 0; all pixels in a ROI of a certain region of interest are defined as a set P={plabel 1, plabel 2, . . . , plabel n}, where n represents a number of pixels, and label represents a mark of a pixel, where 1 refers to positive, and 0 refers to negative;

extracting the local radiomics feature based on the pixel having the biological feature, wherein the local radiomics feature includes a grayscale histogram intensity, a tumor shape feature, a textural feature, a Laplacian of Gaussian (LoG) filtering feature, and a wavelet feature; wherein the extracting the local radiomics feature based on the pixel having the biological feature comprises: traversing all of the pixels in each region of interest of the radiotherapy simulated locating image, and calculating the local radiomics feature values of $\delta \times \delta \times \delta$ neighboring windows of three-dimensional images or $\beta \times \beta$ neighboring windows of two-dimensional images which surrounding each pixel by using each pixel as the center, in which $\delta$ is an odd number greater than or equal to 3, and the $\delta$ value is taken as 3, 5, 7, and 9 respectively each time for the calculation of local radiomics features, such a selection in modeling and verification steps enabling recognition of a $\delta$ value with the optimum accuracy; then a 1×N dimension feature vector of Flabel i={$f_1$(plabel i), $f_2$(plabel i), ..., $f_j$(plabel i)} is obtained for each pixel at a specific δ value, where j∈{1, ..., N}, i∈{1, ..., n}, label∈{1,0} ; for the pixel plabel i, N feature values are extracted, which are $f_1$(p), $f_2$(p_i), ..., $f_j$(p_i) respectively, and are marked as a vector Flabel I, therefore, for all pixels in the ROI, the feature set is 𝓕 {Flabel i, ..., Flabel n}, label∈{1,0}; each pixel serves as one sample with N-dimensional local radiomics features; for pixels on the boundary, symmetric filling is adopted, and the value of the fill pixel is a mirror reflection of the boundary pixel;

acquiring the local radiomics feature to be measured;

identifying a positive region having the local radiomics feature to be measured based on the local radiomics feature; wherein the identifying a positive region having the local radiomics feature to be measured based on the local radiomics feature further comprises:

screening the local radiomics features to determine an optimal feature subset G={$f_1$(p), $f_2$(p), ..., $f_k$(p)}; each labeled pixel and its local radiomics features serve as one sample to participate in feature selection, and both positive and negative pixels participate in this process;

establishing a supervised machine learning model based on the optimal feature subset;

verifying an identification accuracy of the supervised machine learning model based on data of a verification set, and selecting a feature extraction window $δ_{opt}$ that makes the identification accuracy optimal; and identifying a positive region having the local radiomics features to be measured based on the supervised machine learning model; for a new locating image, for which a local radiomics feature-guided radiotherapy plan is to be formulated, the local radiomics features described in the set G are extracted pixel by pixel through a neighboring window having the size of $δ_{opt}$; and the feature parameters of each pixel are input into the supervised machine learning model to output the biological-function expression label of the current pixel; the pixels being positive for the same biological function are labeled with a unified color, and a biological-function positive region being displayed on each tomography image;

performing three-dimensional reconstruction for the peripheral boundary of the positive region to determine a three-dimensional image, wherein the three-dimensional image is a three-dimensional image displaying the biological features; and determining irradiation doses at different locations in different regions based on the three-dimensional image.

2. The method for determining an irradiation dose of claim 1, wherein the extracting the local radiomics feature based on the pixel having the biological feature further comprises:

extracting local radiomics features from pixels having the biological features pixel by pixel through a per-pixel method by adopting a grayscale histogram feature extraction method, a textural feature extraction method, a Laplacian of Gaussian filtering feature extraction method, and a wavelet feature extraction method.

3. The method for determining an irradiation dose of claim 1, wherein the screening the local radiomics features to determine an optimal feature subset further comprises:

screening the local radiomics features through a feature selection method so as to determine an optimal feature subset, wherein the feature selection method comprises Minimum Redundancy-Maximum Relevance.

4. The method for determining an irradiation dose of claim 1, wherein the determining irradiation doses at different locations in different regions based on the three-dimensional image further comprises:

determining an irradiation dose parameter based on the three-dimensional image, wherein the irradiation dose parameter comprises an incident angle, an intensity, and a shape; and determining irradiation doses at different locations in different regions based on the irradiation dose parameter.

5. A system for determining an irradiation dose, comprising a processor configured to:

determine a pixel having a biological feature in a region of interest in a radiotherapy simulated locating image by using a retrospective label, wherein the radiotherapy simulated locating image comprises computed tomography imaging, nuclear magnetic resonance imaging, and positron emission tomography imaging, and the biological feature comprises the glucose metabolism conditions, hypoxic regions, oxygen-enriched regions, angiogenesis conditions in the tumor, and the magnitude of complications risk in normal tissues; wherein the processor is further configured to carry out an image registration between images reflecting biological features of the region of interest and the radiotherapy simulated locating image by retrospective analysis, and then label corresponding pixels in the region of interest of the radiotherapy simulated locating image base on whether pixels in the images reflecting biological features of the region of interest have a biological feature of interest, to determine a pixel having a biological feature in a region of interest in a radiotherapy simulated locating image by using a retrospective label, wherein labeling positive pixel with 1 while labeling negative pixel with 0; all pixels in a ROI of a certain region of interest are defined as a set P={plabel 1, plabel 2, ..., plabel n}, where n represents a number of pixels, and label represents a mark of a pixel, where 1 refers to positive, and 0 refers to negative;

extract a local radiomics feature based on the pixel having the biological feature, wherein the local radiomics feature comprises a grayscale histogram intensity, a tumor shape feature, a Laplacian of Gaussian filtering feature, a textural feature, and a wavelet feature; wherein the processor is further configured to traverse all of the pixels in each region of interest of the radiotherapy simulated locating image, and calculate the local radiomics feature values of δ×δ×δ neighboring windows of three-dimensional images or δ×δ neighboring windows of two-dimensional images which surrounding each pixel by using each pixel as the center, in which δ is an odd number greater than or equal to 3, and the δ value is taken as 3, 5, 7, and 9 respectively each time for the calculation of local radiomics features, such a selection in modeling and verification steps enabling recognition of a δ value with the optimum accuracy; then a 1×N dimension feature vector of Flabel i={$f_1$(plabel i), $f_2$(plabel i), ..., $f_j$(plabel i)} is obtained for each pixel at a specific δ value, where j∈{1, ..., N}, i∈{1, ..., n}, label∈{1,0}; for the pixel plabel i, N feature values are extracted, which are $f_1$(p_i), $f_2$(p_i), ..., $f_j$(p_i) respectively, and are marked as a vector Flabel I, therefore, for all pixels in the ROI, the feature set is $\mathcal{F}$ {Flabel i, ..., Flabel n}, label∈{1,0}, each pixel (label=1/0) serves as one sample with N-dimensional local radiomics features; for pixels on the boundary, symmetric filling is adopted, and the value of the fill pixel is a mirror reflection of the boundary pixel;

acquire the local radiomics features to be measured;

identify a positive region having the local radiomics features to be measured based on the local radiomics features; wherein the processor is further configured to:

screen the local radiomics features to determine an optimal feature subset $G=\{f_1(p), f_2(p), \ldots, f_k(p)\}$; each labeled pixel and its local radiomics features serve as one sample to participate in feature selection, and both positive and negative pixels participate in this process;

establish a supervised machine learning model based on the optimal feature subset;

verify an identification accuracy of the supervised machine learning model based on data of a verification set, and select a feature extraction window $\delta_{opt}$ that makes the identification accuracy optimal; and identify a positive region having the local radiomics features to be measured based on the supervised machine learning model; for a new locating image, for which a local radiomics feature-guided radiotherapy plan is to be formulated, the local radiomics features described in the set G are extracted pixel by pixel through a neighboring window having the size of $\delta_{opt}$; and the feature parameters of each pixel are input into the supervised machine learning model to output the biological-function expression label of the current pixel; the pixels being positive for the same biological function are labeled with a unified color, and a biological-function positive region being displayed on each tomography image;

perform three-dimensional reconstruction for the peripheral boundary of the positive region to determine a three-dimensional image, wherein the three-dimensional image is a three-dimensional image displaying the biological features; and determine irradiation doses at different locations in different regions based on the three-dimensional image.

6. The system for determining an irradiation dose of claim 5, wherein the processor is further configured to:

extract local radiomics features from pixels having the biological features pixel by pixel through a per-pixel method by adopting a grayscale histogram feature extraction method, a textural feature extraction method, a Laplacian of Gaussian filtering feature extraction method, and a wavelet feature extraction method.

7. The system for determining an irradiation dose of claim 5, wherein the processor is further configured to:

screen the local radiomics features through a feature selection method so as to determine an optimal feature subset, wherein the feature selection method comprises Minimum Redundancy-Maximum Relevance.

8. The system for determining an irradiation dose of claim 5, wherein the processor is further configured to:

determine an irradiation dose parameter based on the three-dimensional image, wherein the irradiation dose parameter comprises an incident angle, an intensity, and a shape; and determine irradiation doses at different locations in different regions based on the irradiation dose parameter.

* * * * *